United States Patent [19]

Bechthold et al.

[11] 4,408,478

[45] Oct. 11, 1983

[54] HEATABLE CELL FOR PHOTOACOUSTIC TESTS

[75] Inventors: Paul Bechthold, Pulheim-Dansweiler; Franz Joswig, Jülich; Josef Lingenbach, Düren, all of Fed. Rep. of Germany

[73] Assignee: Kernforschungsanlage Jülich Gesellschaft mit beschränkter Haftung, Jülich, Fed. Rep. of Germany

[21] Appl. No.: 246,034

[22] Filed: Mar. 20, 1981

[30] Foreign Application Priority Data

Mar. 25, 1980 [DE] Fed. Rep. of Germany ... 8008158[U]

[51] Int. Cl.³ .......................................... G01N 21/00
[52] U.S. Cl. ........................................................ 73/24
[58] Field of Search .................. 73/24; 250/343, 351; 356/437, 438, 439

[56] References Cited

U.S. PATENT DOCUMENTS 4,028,932 6/1977 Rosencwaig ............................ 73/24

OTHER PUBLICATIONS

Zharov et al., "Optoacoustic Laser Spectroscopy of Excited Vibrational Molecular States", *Applied Physics,* pp. 15-17, 1977.

*Primary Examiner*—Stephen A. Kreitman
*Attorney, Agent, or Firm*—Becker & Becker, Inc.

[57] ABSTRACT

A heatable cell for photoacoustic tests. The cell includes a specimen chamber which is connected with the microphone chamber of a detector microphone, and is provided with a specimen receiving portion and light admission window located across therefrom. A recess is located in the chamber closure and serves as the specimen receiving portion. The sealing surface of the chamber closure is sealingly pressed against a sealing surface of the chamber. At least one heating winding is provided on the chamber and/or on the chamber closure, and a thin-wall connecting tube having poor heat conducting characteristics is provided between the specimen chamber and the microphone chamber, which is arranged lower than the specimen chamber to prevent convection.

9 Claims, 6 Drawing Figures

HEATABLE CELL FOR PHOTOACOUSTIC TESTS

The present invention relates to a heatable cell for photo- or optoacoustical tests with a specimen or sample chamber which is connected by way of a tube with the microphone chamber of a detector microphone, and is provided with a specimen or sample receiving portion and a light admission or incidence window located across therefrom.

BACKGROUND OF THE INVENTION

The photoacoustical technique is based upon a discovery by A. G. Bell (1880), according to which a substance which is periodically radiated with light emits a sound signal. The application of this effect in more recent times leads to development of "photoacoustic spectroscopy" (see A. Rosencwaig in "Optoacoustic Spectroscopy and Detection" Academic Press 1977) for which devices have been commercially available since 1977.

It is an object of the present invention to provide a heatable cell for this photoacoustic process, which heretofore was conducted at room temperature.

BRIEF DESCRIPTION OF THE DRAWING

This object, and other objects and advantages of the present invention, will appear more clearly from the following specification in connection with the accompanying drawings, in which.

SUMMARY OF THE INVENTION

Figure 1:
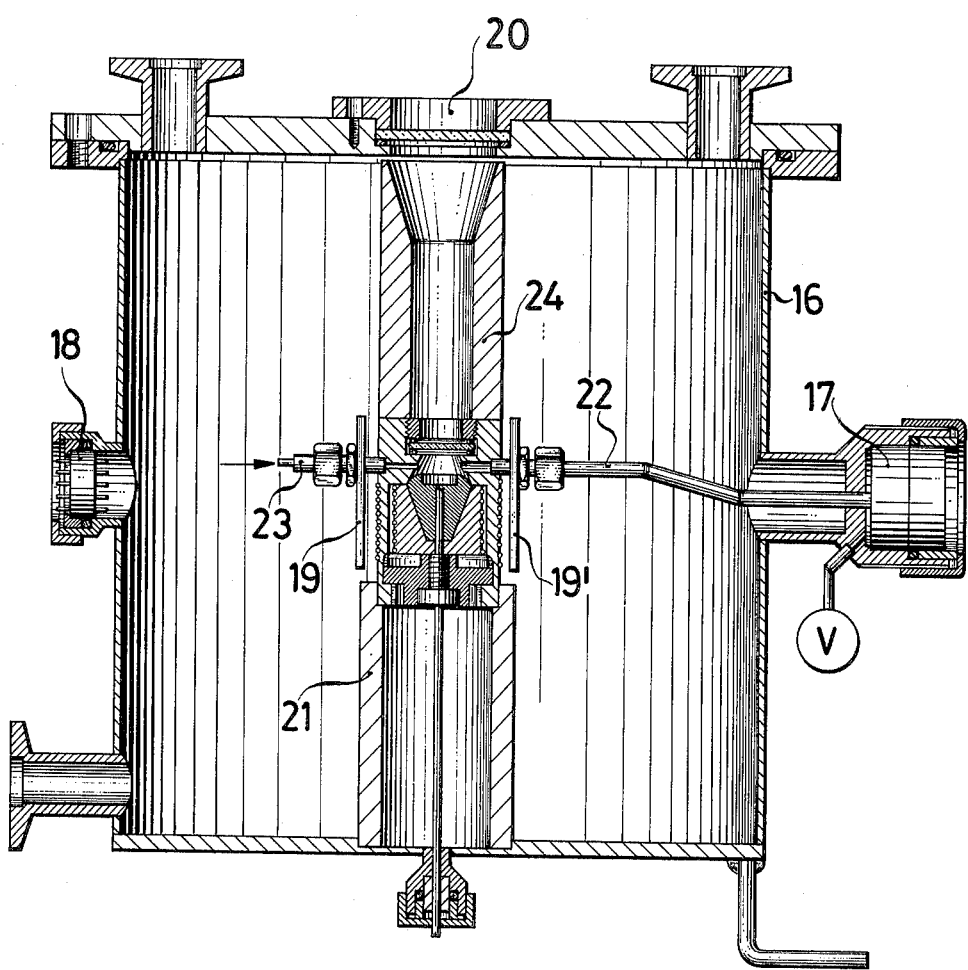
FIG. 1 shows an overall view, partly in section, of one embodiment of a completely assembled inventive cell.

A heatable cell of the initially described type is inventively primarily characterized by a recess located in the chamber closure and serving as the specimen or sample receiving portion; the sealing surface of the chamber closure is sealingly pressed against a sealing surface of the chamber; at least one heating winding is provided on the chamber and/or on the chamber closure, and a thin-walled connecting tube having poor heat conducting properties is provided between the specimen chamber and the microphone chamber, which along with the microphone contained therein, is arranged lower than the specimen chamber to preclude convection.

Such a cell is particularly easy to handle and operates with good temperature constancy or stability, particularly when two heating windings are used.

The chamber and chamber closure especially comprise metal, and the seal of the closure occurs by way of metallic, especially polished metal, sealing surfaces, of which the sealing surface located at the chamber closure is spherical or is a part of a spherical surface, while a conical sealing surface, on which the spherical surface rests, is located on the chamber itself. Preferably, the chamber closure engages from below into the chamber, which at its upper side is provided with a chamber window sealed off by metallic or polyirridic finned rings.

The chamber itself is then extended downwardly to form a sort of sleeve, into which the chamber closure engages. Preferably, this sleeve-like extension and the chamber closure each have a heating winding, and their mass is large compared to the mass of the specimen, thus resulting in an especially good temperature constancy or stability.

The chamber closure is preferably tightened in a sealing manner by a sort of bayonet closure, with a pressure screw, by pressing the closure against the sealing surface of the chamber. The closure is supported on a corresponding projection of the sleeve-like chamber extension. Furthermore, the closure body itself preferably comprises two parts, one of which, the outer part, carries the heating winding, while the inner part is provided with the sealing surface and the recess which serves to receive the specimen. These two parts engage one another along conical contact surfaces.

The chamber is preferably located in a housing, particularly one which is evacuated or flushed by argon, thus providing the housing with a protective atmosphere shielding. In the wall of the housing (somewhat lower than the specimen chamber itself), there is provided a sleeve for receiving the detector microphone, to which a small tube leads from the specimen chamber as far as to the housing wall. Lead-in wires or bushings for the electrical heating of the specimen chamber are furthermore mounted in the housing wall in such a way that they can be easily released from the heating connections from the inside. The specimen chamber itself preferably has two valves for the introduction of gas or for bringing about a pressure constancy or stability during the measurement or testing.

The chamber, inside the housing, can be seated upon a thermally insulating support base or foundation, comprising, for example, ceramic.

DESCRIPTION OF THE PREFERRED EMBODIMENT

Figure 2:
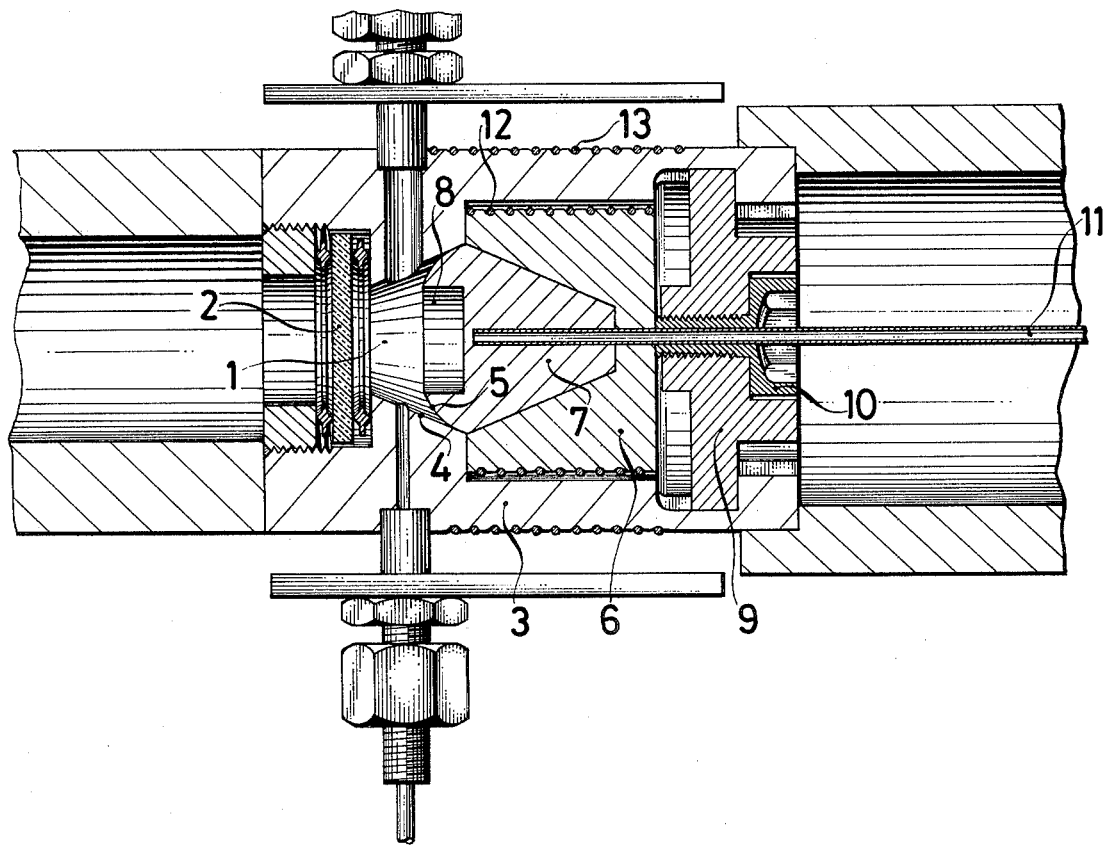
FIG. 2 shows the actual sample chamber of FIG. 1 in an enlarged scale.

Referring now to the drawings in detail, the essential elements of the inventive heatable cell for photoacoustic or optoacoustic purposes shown in FIG. 1 can be recognized even more clearly in FIG. 2. The chamber 1 is delimited on the light admission or incidence side by a window 2 which is inserted in the chamber body 3. The chamber body 3 has a sleeve-like extension across from the window, and has a conical surface 4 at the chamber closure. A spherical surface 5 of a closure element 7, which is provided in the closure body 6, presses against the conical surface 4. This closure element 7 has a recess 8 for receiving the test specimens or samples. The closure body 6,7 is secured in position and tightened by a closing part 9 with a screw 10. The hollow shaft 11 serves for receiving a thermocouple element with which the chamber temperature is monitored. The heating is effected by the two windings 12 and 13 which comprise insulated coaxial heating conductors.

Figure 4:
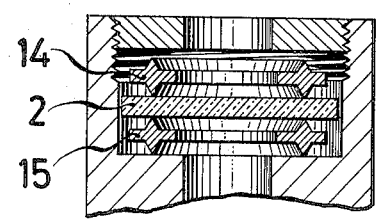
FIG. 4 shows the sealing of the chamber window in a fragmentary view.

In FIG. 4, the window 2 is sealingly assembled between two copper rings 14 and 15 having fins or shoulders resting on the window surface.

As shown in FIG. 1, the entire arrangement described in the foregoing paragraphs is located in an inert gas housing 16, on the wall of which, located opposite the specimen chamber, there is provided a microphone 17. Also provided are lead-in wires or bushings 18 for the electrical heating, as well as heat shields 19, 19' for the heated specimen chamber. A quartz window 20 is located in the light beam or radiation path. The chamber is supported from below by a ceramic base or foundation 21. The connections for the microphone tubes 22 and the gas inlet 23 are easily detachable, so that the entire chamber can be removed readily from the housing 16. A tube or localizer 24 shields the beam path from the surrounding housing.

Figure 3:
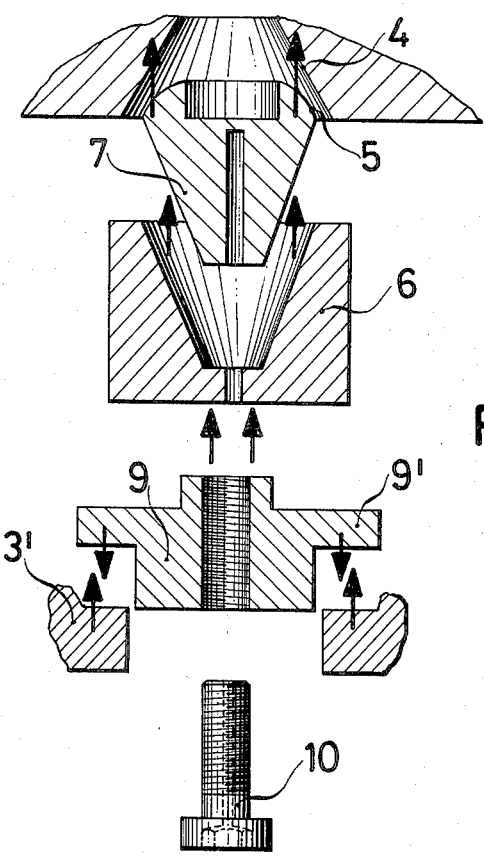
FIG. 3 is an exploded view of the chamber closure.
Figure 3A:
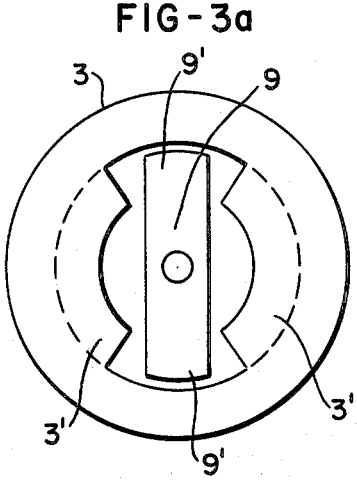
FIG. 3a is an end view of the chamber closure showing the chamber closure in its open position.
Figure 3B:
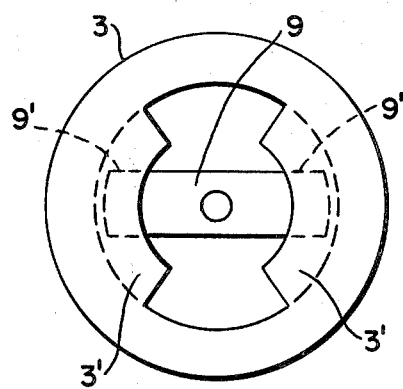
FIG. 3b is an end view of the chamber closing showing its closed position.

The assembly of the chamber closure is apparent from FIG. 3. The spherical surface 5 of the closure element 7 rests upon the conical surface 4 of the chamber, and the other side of the element 7 enters the closure body 6, whereby for improvement of the heat transfer, a conical contact surface is selected. Both elements 6,7 together are pushed against the conical surface 4 by the closing part 9, which is provided with flanges 9', which, after rotation, engage projections 3' of the chamber body 3, which projections 3' are operative as abutments or supports. This is further illustrated by FIGS. 3*a* and 3*b*, wherein FIG. 3*a* shows the chamber closure in its open position, while FIG. 3*b* shows the closed position of the chamber closure, which occurs after the rotation of the closing part 9. The entire arrangement can be sealingly tightened with one screw 10.

The present invention is, of course, in no way restricted to the specific disclosure of the specification and drawings, but also encompasses any modifications within the scope of the appended claims.

What we claim is:

1. A heatable cell arrangement for photoacoustic tests comprising:
   a sample holding chamber including:
   a chamber body forming the side wall of said chamber and having at one end a sealing surface and at its opposite end a light admission window which closes said chamber body;
   a chamber closure having a sealing surface engaging said sealing surface of said chamber body, said chamber closure delimiting that side of said chamber opposite said light admission window, and being provided with a recess for receiving test samples; and
   at least one heating winding provided on at least one of said chamber closure and said chamber body; and
   a detector microphone having a microphone chamber which is arranged lower than said sample holding chamber to preclude convection and which is connected to said sample holding chamber by a thin-walled connecting tube having poor heat-conducting properties.

2. A heatable cell according to claim 1, in which said chamber body and said chamber closure comprise metal, and in which the mass of these two parts is large compared to the mass of a specimen.

3. A heatable cell according to claim 2, in which said sealing surface of said chamber closure is an at least partially spherical polished metal sealing surface, and in which said sealing surface of said chamber body is a conical polished metallic sealing surface.

4. A heatable cell according to claim 1, in which said light admission window delimits said specimen chamber from above, and said chamber closure in said chamber body delimits said specimen chamber from below.

5. A heatable cell according to claim 4, in which said chamber body includes a sleeve-like extension forming an opening which opens in a direction away from said light admission window and which communicates with said specimen chamber, and in which said chamber closure includes a bayonet closure with a pressure screw for pressing said closure against said sealing surface of said chamber body.

6. A heatable cell according to claim 5, which respectively includes a heating winding on said sleeve-like extension of said chamber body and on said chamber closure.

7. A heatable cell according to claim 4, in which said chamber closure includes a first element which is provided with said sealing surface of said chamber closure and with said recess which serves as said specimen receiving portion of said specimen chamber, and a second element which is provided with said heating winding, both of said elements of said chamber closure being provided with conical contact surfaces along which said two elements engage one another.

8. A heatable cell according to claim 1, in which said light admission window is sealingly fixed in position by metallic finned rings which engage said window.

9. A heatable cell according to claim 1, which includes a housing for said chamber body, said housing being provided for a protective atmosphere shielding.

* * * * *